United States Patent
Hanke et al.

(10) Patent No.: US 8,229,061 B2
(45) Date of Patent: Jul. 24, 2012

(54) X-RAY COMPUTER TOMOGRAPH AND METHOD FOR INVESTIGATING A COMPONENT BY MEANS OF X-RAY COMPUTER TOMOGRAPHY

(75) Inventors: Randolf Hanke, Puschendorf (DE); Theobald Fuchs, Nürnberg (DE); Tobias Schön, Nürnberg (DE); Michael Maisl, Freisen (DE); Stefan Kasperl, Erlangen (DE)

(73) Assignee: Fraunhofer-Gesellschaft zur Förderung der angewandten Forschung e.V., München (DE)

( * ) Notice: Subject to any disclaimer, the term of this patent is extended or adjusted under 35 U.S.C. 154(b) by 0 days.

(21) Appl. No.: 12/989,590

(22) PCT Filed: Apr. 21, 2009

(86) PCT No.: PCT/EP2009/002893
§ 371 (c)(1),
(2), (4) Date: Oct. 25, 2010

(87) PCT Pub. No.: WO2009/129994
PCT Pub. Date: Oct. 29, 2009

(65) Prior Publication Data
US 2011/0103546 A1    May 5, 2011

(30) Foreign Application Priority Data
Apr. 25, 2008   (DE) .................. 10 2008 020 948

(51) Int. Cl.
*A61B 6/00*   (2006.01)

(52) U.S. Cl. ............................................. 378/20; 378/4
(58) Field of Classification Search ............... 378/4, 20
See application file for complete search history.

(56) References Cited

U.S. PATENT DOCUMENTS

| | | | |
|---|---|---|---|
| 5,023,895 A | 6/1991 | McCroskey et al. | |
| 5,345,490 A | 9/1994 | Finnigan et al. | |
| 5,740,224 A | 4/1998 | Muller et al. | |
| 6,435,714 B1 * | 8/2002 | Bruder | 378/196 |
| 6,459,756 B1 * | 10/2002 | Tam et al. | 378/15 |

(Continued)

FOREIGN PATENT DOCUMENTS

DE   103 04 662 A1   8/2004

(Continued)

OTHER PUBLICATIONS

Sourbelle, Katia, Performance Evaluation of Exact and Approximate Cone-Beam Algorithms in Spiral Computed Tomography, 2002, pp. 1-113, Shaker Verlag, Aachen, Germany.

*Primary Examiner* — Edward Glick
*Assistant Examiner* — Alexander H Taningco
(74) *Attorney, Agent, or Firm* — McGlew and Tuttle, P.C.

(57) ABSTRACT

In an X-ray computer tomograph and a method for examining a component by means of X-ray computer tomography, the component carries out a movement relative to a radiation source detector unit in at least two degrees of freedom of movement, so at least one trajectory can be produced which spans a three-dimensional space. Since the X-radiation has a three-dimensional radiation geometry, volume data can be rapidly obtained and precisely reconstructed to form a three-dimensional X-ray image. The component can be geometrically measured by means of a geometry detection unit.

26 Claims, 4 Drawing Sheets

U.S. PATENT DOCUMENTS

| | | | |
|---|---|---|---|
| 6,811,313 B2 | 11/2004 | Graumann et al. | |
| 7,298,815 B2 | 11/2007 | Yoshino | |
| 7,450,682 B2 * | 11/2008 | Schonborn et al. | 378/4 |
| 7,561,659 B2 * | 7/2009 | Cho et al. | 378/13 |
| 7,568,837 B2 * | 8/2009 | Heigl et al. | 378/207 |
| 7,711,083 B2 * | 5/2010 | Heigl et al. | 378/20 |
| 2002/0141628 A1 * | 10/2002 | Bruder et al. | 382/131 |
| 2002/0186819 A1 * | 12/2002 | Proksa | 378/207 |
| 2003/0012331 A1 * | 1/2003 | Kojima et al. | 378/4 |
| 2003/0035513 A1 * | 2/2003 | Horiuchi | 378/210 |
| 2003/0128869 A1 | 7/2003 | Grass et al. | |
| 2004/0017882 A1 * | 1/2004 | Misawa et al. | 378/4 |
| 2004/0109532 A1 | 6/2004 | Ford et al. | |
| 2004/0258200 A1 * | 12/2004 | Tsujii | 378/62 |
| 2005/0180544 A1 * | 8/2005 | Sauer et al. | 378/195 |
| 2005/0243963 A1 * | 11/2005 | Ghelmansarai et al. | 378/7 |
| 2006/0050842 A1 * | 3/2006 | Wang et al. | 378/16 |
| 2006/0083345 A1 * | 4/2006 | Hsieh et al. | 378/17 |
| 2006/0222148 A1 * | 10/2006 | Boese et al. | 378/179 |
| 2007/0053489 A1 * | 3/2007 | Lu et al. | 378/62 |
| 2007/0189453 A1 | 8/2007 | Yang et al. | |

FOREIGN PATENT DOCUMENTS

| | | |
|---|---|---|
| EP | 0 875 751 A1 | 11/1998 |
| JP | 63085481 A * | 4/1988 |
| JP | 01211900 A * | 8/1989 |
| WO | WO 00/46592 A | 8/2000 |
| WO | WO 03/085416 A | 10/2003 |

* cited by examiner

X-RAY COMPUTER TOMOGRAPH AND METHOD FOR INVESTIGATING A COMPONENT BY MEANS OF X-RAY COMPUTER TOMOGRAPHY

CROSS REFERENCE TO RELATED APPLICATIONS

This application is a United States National Phase application of International Application PCT/EP2009/002893 and claims the benefit of priority under 35 U.S.C. §119 of German Patent Application DE 10 2008 020 948.1 filed Apr. 25, 2008, the entire contents of which are incorporated herein by reference.

FIELD OF THE INVENTION

The invention relates to an X-ray computer tomograph for examining a component by means of X-ray computer tomography. The invention furthermore relates to a method for examining a component by means of X-ray computer tomography.

BACKGROUND OF THE INVENTION

X-ray computer tomography (CT) is used in the industrial sector for destruction-free and contact-less examination of components. X-ray computer tomography, for example, allows the detection of material defects and their characterization with regard to their type and position in the component. Moreover, there is a need on the part of the industry to geometrically measure the component by means of X-ray computer tomography, so the adherence to manufacturing tolerances, in particular in the case of concealed inner structures of the component, can be checked.

In known methods for the examination and geometric measurement of components, the component to be examined is irradiated with X-radiation in the form of a substantially two-dimensional fan beam with the component rotating once during the irradiation. Fan beam data of the irradiated, substantially two-dimensional layer of the component are measured by means of a single- or multi-line detector. The multi-line detectors used have a substantially smaller line number than column number, for example 16 lines to 1024 columns. The irradiated two-dimensional layer of the component can be precisely reconstructed from the fan beam data. A method of this type is known, for example, from EP 0 875 751 A1. The drawback in this method is that to obtain three-dimensional volume data of the component, a considerable expenditure of time is required as the component has to be detected layer by layer. Because of the time expenditure required this method is unsuitable for an industrial geometric measurement of components.

SUMMARY OF THE INVENTION

The invention is therefore based on the object of providing an X-ray computer tomograph which allows a rapid and precise geometric measurement of a component.

This object is achieved according to the invention by an X-ray computer tomograph for examining a component by means of X-ray computer tomography, comprising
   a radiation source detector unit, comprising
      a radiation source for producing X-radiation with a three-dimensional radiation geometry, and
      a planar detector for detecting the X-radiation,
   a component carrier for positioning a component to be examined between the radiation source and the planar detector, and
   a computing device for evaluating the detected X-radiation
wherein
   the radiation source detector unit and the component carrier have at least two degrees of freedom of movement relative to one another in such a way that at least one trajectory spanning a three-dimensional space is producible,
   the computing device
      has a reconstruction unit for reconstructing a three-dimensional X-ray image of the component from the X-radiation detected along the at least one trajectory, and
      has a geometry detection unit for determining dimensional measurement data of the component from the three-dimensional X-ray image.

It was recognized according to the invention that volume data of a component to be examined can be obtained rapidly by means of X-radiation with a three-dimensional radiation geometry and can be reconstructed to form a precise three-dimensional X-ray image of the component if the radiation source detector unit and the component carrier carry out a movement relative to one another in at least two degrees of freedom of movement so at least one trajectory spanning a three-dimensional space is produced. The path which a focal spot of the radiation source takes relative to the component to be examined during irradiation with X-radiation is called the trajectory. Because of the two degrees of freedom of movement, for example, a helical trajectory (spiral path or helix path) or/and two circular trajectories inclined with respect to one another, in particular perpendicularly, can be produced. Since the radiation source produces X-radiation with a three-dimensional radiation geometry, which is detected by means of a multi-line detector configured as a planar detector, volume data of the component can be rapidly obtained without the component having to be detected layer by layer. Planar detectors are taken to mean detectors with a ratio of detector height to detector width of at least ⅛, in particular of at least ¼, and in particular of ½, for example a multi-line detector with 256 lines and 1024 columns. The terms detector height and detector width are to be understood such that the detector height can be at most as great as the detector width. The volume data obtained in this manner can be reconstructed by means of the reconstruction unit to form a precise three-dimensional X-ray image. In particular, the volume data measured by means of the planar detector are converted by means of the reconstruction unit directly into the volume units (voxels) of the three-dimensional X-ray image, so an impairment of the image quality due to intermediate steps, such as, for example, the reconstruction and the joining of individual layers of the component, can be avoided. The image quality is homogeneous and isotropic over the entire component. No impairment of the image quality with an increasing cone angle occurs. Since the image quality over the entire component is homogeneous and isotropic, dimensional measurement data can be determined independently of the site with high precision by means of the geometry detection unit. For example, the adherence to manufacturing tolerances of the component can be checked. The X-ray computer tomograph according to the invention thus allows a rapid and precise geometric measurement, in particular of inner and concealed structures, of the component.

A geometry detection unit being configured in such a way that a component surface of the component is determinable, allows dimensional measurement data of the component to be easily determined. The component surface is determined, for example, in such a way that a density value is allocated to each volume unit (voxel) of the three-dimensional X-ray image, the component surface being produced as an area with the same density values. The component surface as a transition between material and air can easily be found in this manner. In particular, the inner component surface, which is not accessible to measurement in a conventional manner, can be determined by means of the geometry detection unit.

A geometry detection unit being configured in such a way that the component surface is determinable from connected triangular areas, optimizes the storage and computing outlay when determining the component surface. The component surface can be determined adequately precisely and with a low outlay for storage and computing by means of connected triangular areas.

A component carrier being rotatably drivable about a rotational axis as one degree of freedom of movement, allows a rotary movement of the component to be examined.

A component carrier being drivable in a translatory manner along the rotational axis as a further degree of freedom of movement, allows a translatory movement of the component to be examined. In particular, a helical trajectory can be produced by a simultaneous rotary movement and translatory movement of the component to be examined.

A component carrier being displaceable along a helical trajectory in such a way that a ratio of feed per rotation to beam widening along the rotational axis is less than 1.5, in particular less than 1, in particular less than 0.85, and in particular less than 0.7, allows the reconstruction of three-dimensional X-ray images with a high resolution and therefore extremely precise determination of dimensional measurement data of the component. The ratio of feed per rotation to beam widening along the rotational axis is called the pitch, in particular the relative pitch, and is a measure of the steepness of the helical trajectory. The smaller the pitch, the more precise the resolution of the three-dimensional X-ray image. Beam widening is taken to mean the widening of the detectable X-radiation along the rotational axis.

A reconstruction unit being configured in such a way that the X-ray image is reconstructable from the X-radiation detected along a helical trajectory, ensures the reconstruction of the three-dimensional X-ray image when the volume data are obtained by movement along a helical trajectory.

A component carrier being pivotable about a pivot axis running transverse to the rotational axis as a further degree of freedom of movement, allows a plurality of trajectories which are inclined with respect to one another to be produced.

A reconstruction unit being configured in such a way that the X-ray image is reconstructable from the X-radiation detected along two circular trajectories inclined with respect to one another, ensures the reconstruction of the three-dimensional X-ray image where the volume data are obtained by movement along two circular trajectories which are inclined with respect to one another.

A component carrier being displaceable along a longitudinal axis between the radiation source and the planar detector, allows projections to be produced with a desired magnification. The closer the component to be examined is arranged to the radiation source, the larger the projection of the component on the planar detector. A projection of the component with a magnification of more than 2, in particular of more than 10, and in particular of more than 50 can advantageously be produced.

A radiation source detector unit being configured in such a way that a radiation source detector spacing is changeable, allows components of different sizes to be examined.

A radiation source having a cone opening angle of more than 10°, in particular of more than 30°, and in particular of more than 50°, allows volume data of the component to be rapidly obtained. The radiation source is advantageously configured in such a way that the cone opening angle can be adjusted.

A radiation source having an accelerating voltage of at least 150 kV, in particular of at least 450 kV, and in particular of at least 900 kV, allows the X-raying of a large number of different components. With an increasing accelerating voltage, relatively large volumes of components can be examined. In particular, with increasing accelerating voltage, metallic components can also be examined. Depending on the desired accelerating voltage, X-ray tubes or linear accelerators can be used as the radiation source. Linear accelerators are used, in particular, at accelerating voltages of more than 900 kV.

A planar detector being pivotable about a pivot axis running transverse thereto, allows the orientation of the planar detector with respect to the at least one trajectory. With a helical trajectory, the planar detector can be oriented in accordance with the pitch, in other words the steepness of the helical trajectory, so the line or column direction is oriented along a tangent of the helical trajectory. Owing to the orientation, the planar detector is optimally utilized, on the one hand, and, on the other hand, the reconstruction of the detected X-radiation to form a three-dimensional X-ray image is simplified. In particular, with a corresponding orientation of the planar detector, an interpolation of the detected X-radiation—as would be necessary without an orientation—between the individual pixels of the planar detector, is not necessary, so a high resolution is achieved. Furthermore, the filter operation, which is indispensable during the reconstruction and has to be carried out in a predetermined direction with respect to the planar detector, can be applied directly to the primarily measured data—without previous sorting and/or interpolation—because of the orientation. A high image quality is also achieved by this. This applies accordingly with a plurality of trajectories inclined with respect to one another.

A reconstruction unit being configured in such a way that each volume unit of the X-ray image is reconstructed directly from volume data recorded by means of the planar detector on X-rays of the type which ran at the point corresponding to the volume unit, ensures a rapid and precise reconstruction the three-dimensional X-ray image. Each volume unit (voxel) of the three-dimensional X-ray image is calculated directly from measured volume data on X-rays of the type which ran through the component or the component surroundings at the point corresponding to the volume unit. This ensures that during the reconstruction of the X-ray image, no intermediate steps, such as, for example, the reconstruction and joining of substantially two-dimensional layers and/or the interpolation or approximation of volume units from measurement data on X-rays, which ran through the component or the component surroundings at points adjacent to the volume unit, are necessary. Thus, a loss of precision during the reconstruction is avoided and a high image quality is achieved. This also applies, in particular, to cone opening angles according to the invention.

The invention is also based on the object of providing a method for examining a component by means of X-ray computer tomography which allows a rapid and precise geometric measurement of a component.

This object is achieved according to the invention by a method for examining a component by means of X-ray computer tomography, comprising the steps:

positioning a component to be examined between a radiation source and a planar detector of a radiation source detector unit, irradiating the component with X-radiation by means of the radiation source, the X-radiation having a three-dimensional radiation geometry, detecting the X-radiation by means of the planar detector, and evaluating the detected X-radiation by means of a computing device wherein the radiation source detector unit (3) and the component (2) carry out a movement relative to one another in at least two degrees (F.) of freedom of movement, in that at least one trajectory spanning a three-dimensional space is produced, a three-dimensional X-ray image of the component is reconstructed from the X-radiation detected along the at least one trajectory by means of a reconstruction unit of the computing device, and dimensional measurement data of the component are determined from the three-dimensional X-ray image by means of a geometry detection unit of the computing device.

The advantages of the method according to the invention correspond to the advantages of the X-ray computer tomograph according to the invention already described.

The various features of novelty which characterize the invention are pointed out with particularity in the claims annexed to and forming a part of this disclosure. For a better understanding of the invention, its operating advantages and specific objects attained by its uses, reference is made to the accompanying drawings and descriptive matter in which preferred embodiments of the invention are illustrated.

DESCRIPTION OF THE PREFERRED EMBODIMENTS

Figure 1:
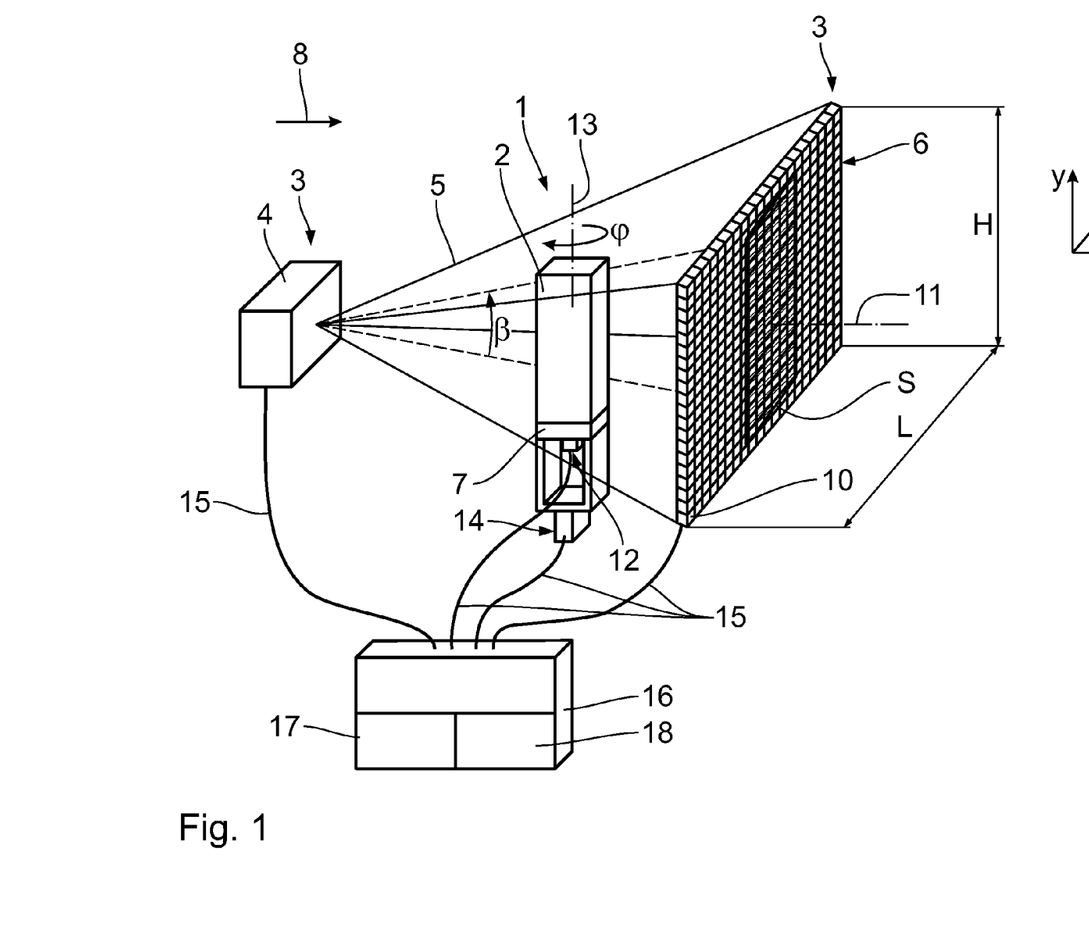
FIG. 1 is a perspective schematic view of an X-ray computer tomograph according to a first embodiment.
Figure 2:
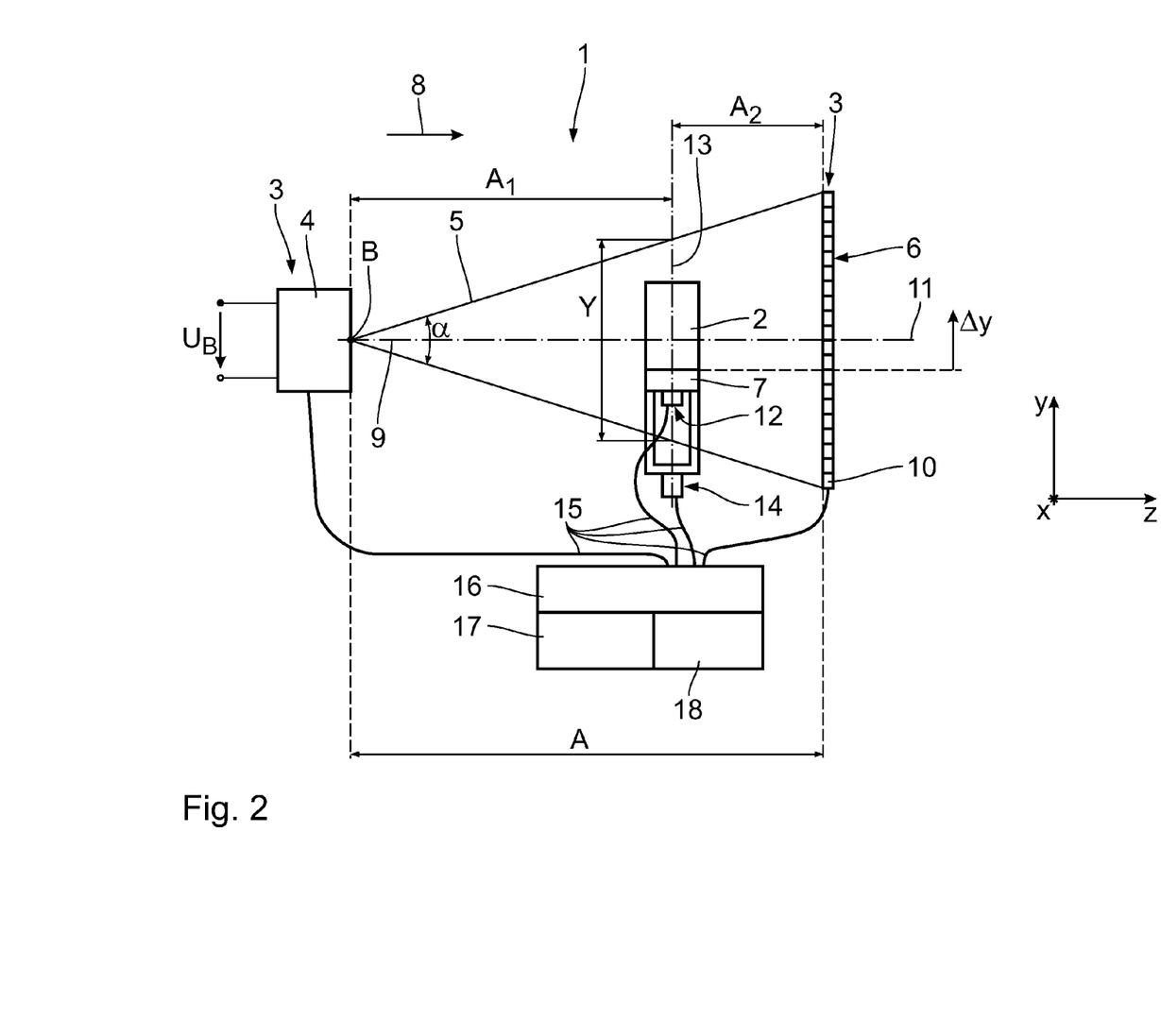
FIG. 2 is a side view of the X-ray computer tomograph in FIG. 1.

A first embodiment of the invention will be described below with reference to FIGS. 1 and 3. An X-ray computer tomograph 1 has a radiation source detector unit 3 to examine a component 2. The radiation source detector unit 3 comprises a radiation source 4 for producing X-radiation 5 and a planar detector 6 for detecting the X-radiation 5. A component carrier 7, on which the component 2 to be examined can be positioned, is arranged between the radiation source 4 and the planar detector 6.

The X-radiation 5 with a three-dimensional radiation geometry, in particular with a conical radiation geometry, can be produced by means of the radiation source 4. The radiation source 4, to irradiate the component 2, has a cone opening angle α of more than 10°, in particular of more than 30°, and in particular of more than 50°. The cone opening angle α is defined in a y-z plane, which is formed by a y-direction and a z-direction running perpendicular thereto. The cone opening angle α of the radiation source 4 may be adjustable. Moreover, the radiation source 4 has a fan beam angle β, which is defined in an x-z plane. The x-z plane is formed by an x-direction, which runs perpendicular to the y-direction and the z-direction, and the z-direction. The fan beam angle β is 52°, for example. The radiation source 4 is configured in such a way that the X-radiation 5 can be emitted in a beam direction 8, the beam direction 8 running substantially along a longitudinal axis 9 of the X-ray tomograph 1. The radiation source 4 has an accelerating voltage $U_B$, which is at least 150 kV, in particular at least 450 kV, and in particular at least 900 kV. The radiation source 4 is configured dependent on the accelerating voltage $U_B$ as an X-ray tube or as a linear accelerator (LINAC), linear accelerators being used at accelerating voltages $U_B$ of more than 900 kV. The structure of an X-ray tube and a linear accelerator is known in principle.

The planar detector 6 substantially extends in an x-y plane, which is formed by the x-direction and the y-direction. The longitudinal axis 9 runs parallel to the z-direction and perpendicular to the x-y plane. The planar detector 6 is configured as a multi-line detector and has a large number of pixels 10 in the x- and y-direction. The pixels 10 define columns in the x-direction and lines in the y-direction. A detector height H is produced in the y-direction from the line number and the size of the pixels 10. Accordingly, a detector width L is produced from the column number and the size of the pixels 10 in the x-direction. The planar detector 6 has a ratio of the detector height H to the detector width L of at least ⅛, in particular of at least ¼, and in particular of ½. For example, the planar detector 6 has 256 lines and 1024 columns, so a ratio of detector height H to detector width L of ¼ is produced. The planar detector 6 can be pivoted about a pivot axis 11. The pivot axis 11 runs perpendicular and centrally with respect to the planar detector 6, so the pivot axis 11 coincides with the longitudinal axis 9. The radiation source 4 and the planar detector 6 define a radiation source detector spacing A in the z-direction. The radiation source detector unit 3 is configured in such a way that the radiation source detector spacing A can be varied. For this purpose, either the radiation source 4 or the planar detector 6 or both can be displaced along the longitudinal axis 9.

The component carrier 7 can be rotatably driven to rotate the component 2 to be examined by means of a first drive device 12 about a rotational axis 13. The rotational axis 13 of the component carrier 7 runs substantially parallel to the y-direction. The rotational axis 13 provides a first degree $F_1$ of freedom of movement. Furthermore, the component carrier 7 can be driven in a translatory manner by means of a second drive unit 14 along the rotational axis 13. This provides a second degree $F_2$ of freedom of movement. The drive devices 12, 14 are electrical, for example.

The rotational axis 13 divides the radiation source detector spacing A into a first spacing $A_1$ and a second spacing $A_2$. The first spacing $A_1$ is produced as the spacing of the radiation source 4 from the rotational axis 13. The second spacing $A_2$ is accordingly produced as the spacing of the rotational axis 13 from the planar detector 6. The component carrier 7 can be displaced to produce a projection S with the desired magnification V along the longitudinal axis 9 between the radiation source 4 and the planar detector 6. The magnification V is produced from the ratio of the radiation source detector spacing A to the first spacing $A_1$.

The X-ray computer tomograph 1 is configured in such a way that the component carrier 7 can be displaced along a helical trajectory. This means that a focal spot B of the radiation source 4 relative to the component carrier 7 or the component 2 arranged on the component carrier 7 can describe a helical path. The component carrier 7 can be displaced along the helical trajectory in such a way that a ratio P of the feed Δy per rotation along the rotational axis 13 to the beam widening Y of the X-radiation 5 which can be detected on the planar detector 6 along the rotational axis 13 is less than 1.5, in particular less than 1, in particular less than 0.85, and in particular less than 0.7. This ratio is also called the pitch P or relative pitch P. The pitch P is therefore a measure of the steepness of the helical trajectory. A pitch P of 1 means, for example, that the component carrier 7 per rotation is displaced by the beam widening Y. The beam widening Y may at most be as great as the ratio of the detector height H to the magnification V.

The radiation source detector unit 3 and the drive devices 12, 14 are connected by signal lines 15 to the computing device 16. The computing device 16 is used to control the X-ray computer tomograph 1 and to evaluate the detected X-radiation 5.

The computing device 16 comprises a reconstruction unit 17 and a geometry detection unit 18. The reconstruction unit 17 is configured in such a way that a three-dimensional X-ray image of the component 2 to be examined can be reconstructed from the X-radiation 5 detected along the helical trajectory. For this purpose, a helix reconstruction algorithm is implemented in the reconstruction unit 17. A reconstruction algorithm of this type in known in principle and described, for example, in the dissertation "Performance Evaluation of Exact and Approximate Cone-Beam Algorithms in Spiral Computed Tomography" by Katia Sourbelle, Shaker Verlag, Aachen, 2002, the entire contents of which are incorporated herein by reference.

The geometry detection unit 18 is used to determine dimensional measurement data M of the component 2 to be examined from the reconstructed three-dimensional X-ray image. The geometry detection unit 18 is configured in such a way that a component surface of the component 2 can be determined. The component surface can be determined, in particular, from connected triangular areas.

The rotational position of the component carrier 7 and therefore of the component 2 is characterized by a rotational angle ϕ. The rotational angle ϕ is a measure of the respective projection direction.

The geometric measurement of the component 2 by means of the X-ray computer tomograph 1 according to the invention will be described below.

The component 2 to be examined is arranged on the component carrier 7. The component 2 is made of plastics material or metal, for example. The radiation source detector spacing A and the cone opening angle α are adjusted and the component carrier 7 is positioned in a desired position in the z-direction depending on the size of the component 2 and the desired magnification V of the projection S.

To produce a helical trajectory, using the computing device 16, a pitch P is adjusted, according to which a helical trajectory with a desired steepness can be produced. In accordance with the pitch P, the planar detector 6 is pivoted about the pivot axis 11 so the planar detector 6 is oriented tangentially with respect to the helical trajectory. After the orientation, the lines of the planar detector 6 thus have a steepness corresponding to the steepness of the helical trajectory.

The component 2 is irradiated with X-radiation 5 by means of the radiation source 4, the X-radiation 5 exiting conically with the desired cone opening angle α. The irradiation takes place, depending on the material and the size of the component 2, with an accelerating voltage $U_B$ of more than 150 kV, in particular of more than 450 kV, and in particular of more than 900 kV.

During the irradiation, the computing device 16 activates the drive devices 12, 14 in such a way that the component carrier 7 is simultaneously rotated about the rotational axis 13 and is moved in a translatory manner along the rotational axis 13 in the y-direction. The component 2 is thus moved relative to the focal spot B of the radiation source 4 along a helical trajectory, the helical trajectory having a steepness corresponding to the adjusted pitch P. The number of required rotations about the rotational axis 13 is produced from the size of the component 2 in the y-direction, the beam widening Y and the pitch P.

The X-radiation 5 is detected by means of the planar detector 6 and converted into digital volume data. The volume data are supplied to the computing device 16. A three-dimensional X-ray image of the component 2 is reconstructed from the volume data by means of the reconstruction unit 17. For this purpose, the volume data are firstly filtered in the tangential direction to the helical trajectory. Owing to the oriented planar detector 6, this filtering can be carried out along the pixels 10 of a line so an additional interpolation step between the pixels 10, as would be necessary with a non-oriented planar detector 6, is dispensed with. The achievable resolution is therefore not impaired by the filtering. The filtered volume data are fed to the helix reconstruction algorithm and converted into a three-dimensional X-ray image.

Figure 3:
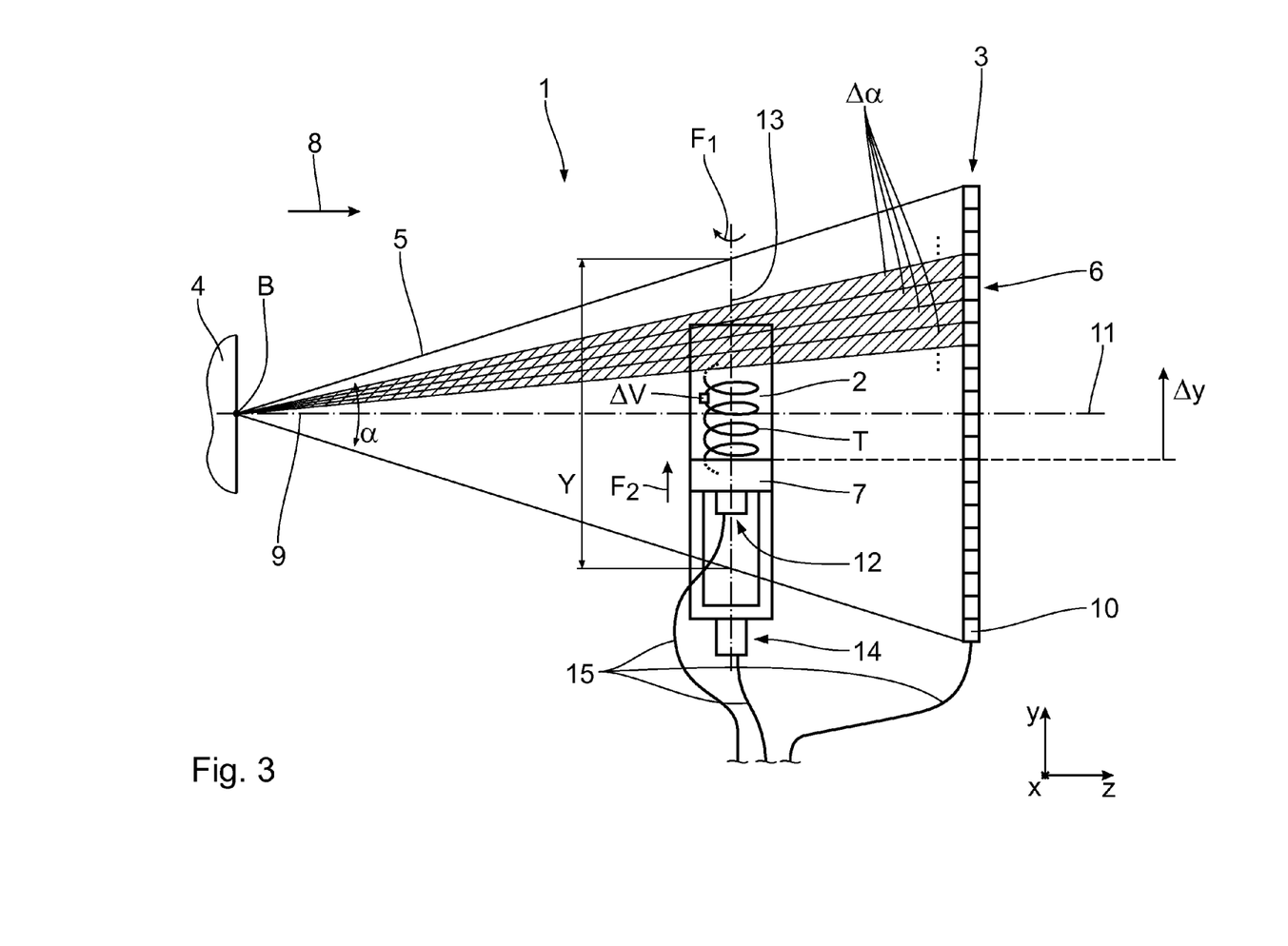
FIG. 3 is a side view of an enlarged detail of the X-ray computer tomograph in FIG. 2.

The reconstruction of the three-dimensional X-ray image from the volume data is shown in principle in FIG. 3. FIG. 3 shows, by way of example, radiation regions Δα, in which X-rays run, which impinge on the planar detector 6 in the region of a pixel 10 and produce corresponding volume data for the projection position shown in FIG. 3. During the reconstruction, each volume unit (voxel) of the three-dimensional X-ray image is calculated directly and exclusively from volume data on X-rays of the type which ran through the component 2 or the component surroundings at the point corresponding to the volume unit. In other words, for example, a specific point of the component 2—designated ΔV in FIG. 3—during its helical relative movement T with respect to the focal spot B, runs through a plurality of radiation regions Δα, in which the X-rays run through this point in the component 2 and produce corresponding volume data. During the reconstruction of the volume unit corresponding to this point, these volume data are directly converted into the volume unit. Intermediate steps, such as, for example, the reconstruction and joining of layers of the component 2, are not necessary, so the reconstruction of the X-ray image is possible rapidly and with a high degree of precision.

During the evaluation of the X-ray image, already faulty inner structures of the component 2 can be localized and characterized.

Dimensional measurement data M of inner structures of the component 2, such as, for example, lengths, areas or undesired deviations from a desired form, are determined by means of the geometry detection unit 18 from the reconstituted X-ray image. The geometry detection unit 18 firstly determines the component surface of the component 2. The component surface is composed of the outer and the inner—not accessible—component surface. For this purpose, a density value is allocated to each volume unit (voxel) of the three-dimensional X-ray image. With the aid of the density values, the material of the component 2 can be distinguished from the surrounding air, so the component surface is produced as an area with the same density values. The component surface is then approximated by mutually connected triangles, so the storage and computing outlay for the geometric measuring of the component surface is optimized. The triangular areas are determined in such a way that all the volume units of the three-dimensional X-ray image are run through, wherein for the volume units, which are intersected by the area of the same density values, the partial area contained therein is approximated by triangular areas. The dimensional measurement data M can then be obtained from the component surface.

A second embodiment of the invention will be described below with reference to FIG. 4. Structurally identical parts receive the same reference numerals as in the first embodiment, to the description of which reference is hereby made. Structurally different, but functionally similar parts receive the same reference numerals with an a placed thereafter. The important difference compared to the first embodiment is that the component carrier 7a of the X-ray computer tomograph 1a can be pivoted about a pivot axis 19 running parallel to the longitudinal axis 9 by means of the drive device 14a, as the second degree $F_2$ of freedom of movement. In addition, the component carrier 7a can be displaced—in accordance with the first embodiment—along the rotational axis 13, as the third degree $F_3$ of freedom of movement. The pivot axis 19 runs perpendicular to the rotational axis 13, so a plurality of circular trajectories which are inclined relative to one another can be produced. The reconstruction unit 17a of the computing device 16a is configured in such a way that a three-dimensional X-ray image can be reconstructed from the X-radiation 5 detected along two circular trajectories inclined with respect to one another.

Figure 4:
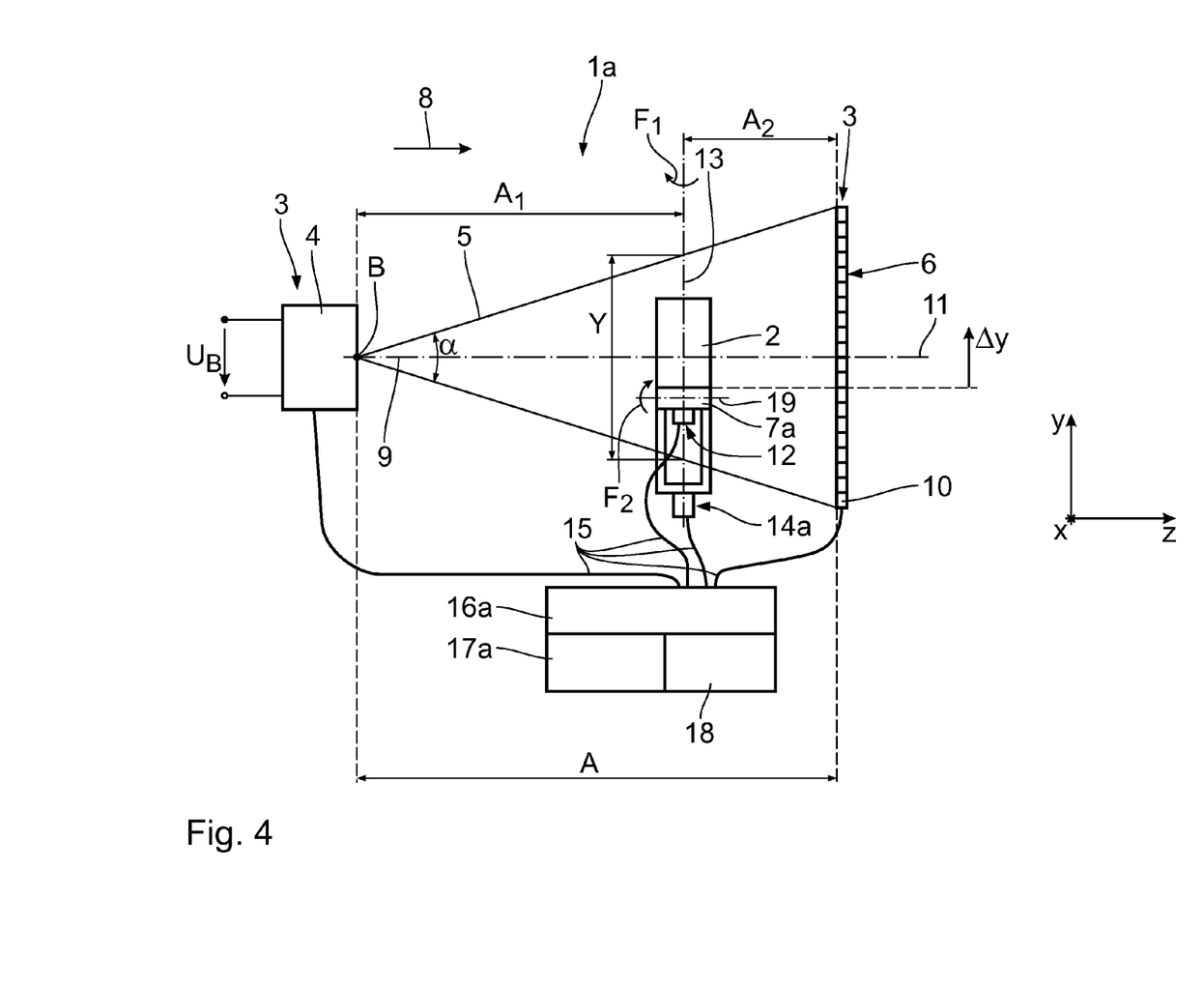
FIG. 4 is a side view of an X-ray computer tomograph according to a second embodiment.

The component carrier 7a is firstly located in the position shown in FIG. 4 to irradiate the component 2. In this position, the component carrier 7a is rotated once about the rotational axis 13 by means of the drive device 12, so the component 2 is moved relative to the focal spot B along a first circular trajectory. The volume data thus obtained are supplied to the computing device 16a. The component carrier 7a is then pivoted by means of the drive device 14a through 90° about the pivot axis 19. In this position, the component 2 is irradiated again and rotated once about the rotational axis 13 pivoted through 90°. The planar detector 6 can be pivoted about the pivot axis 11 in accordance with the component carrier 7a, so the volume data obtained during the renewed irradiation can be simply reconstructed by means of the reconstruction unit 17a into a three-dimensional X-ray image. The volume data obtained during the renewed irradiation are supplied to the computing device 16a. During the renewed irradiation of the component 2, the latter is moved relative to the focal spot B along a second circular trajectory, the second trajectory being inclined through 90° relative to the first trajectory. From the volume data, the reconstruction unit 17a reconstructs a three-dimensional X-ray image, which, corresponding with the first embodiment, allows a geometric measuring of the component 2 by means of the geometry detection unit 18.

With regard to the further mode of functioning, in particular the reconstruction of the three-dimensional X-ray image, reference is made to the first embodiment.

The invention thus allows an enormous increase in speed in comparison to geometric measuring of the component 2 by means of a two-dimensional fan beam in conjunction with high measuring precision. In particular, in comparison to examination of the component 2 by means of a three-dimensional cone beam with exclusively a rotation of the component 2, in other words with a trajectory spanning only a two-dimensional space, the proportion of cone beam artefacts, which are unavoidable in field camp-like reconstruction algorithms, is significantly reduced and the geometric precision of the reconstruction, in particular outside the central radiation plane, is significantly improved. The geometric resolution is homogeneous and isotropic for the entire component 2. The invention therefore allows the use of dimensional measuring technology (metrology) in industrial applications, as dimensional measurement data can be determined rapidly and independently of site with a high degree of precision.

While specific embodiments of the invention have been described in detail to illustrate the application of the principles of the invention, it will be understood that the invention may be embodied otherwise without departing from such principles.

The invention claimed is:

1. An X-ray computer tomograph for examining a component by means of X-ray computer tomography, comprising:
    a radiation source detector unit, comprising a radiation source for producing X-radiation with a three-dimensional radiation geometry, and a planar detector for detecting the X-radiation;
    a component carrier for positioning a component to be examined between the radiation source and the planar detector; and
    a computing device for evaluating the detected X-radiation, wherein the radiation source detector unit and the component carrier have at least two degrees of freedom of movement relative to one another in such a way that at least one trajectory spanning a three-dimensional space is producible, said computing device having a reconstruction unit for reconstructing a three-dimensional X-ray image of the component from the X-radiation detected along the at least one trajectory, and said computing device having a geometry detection unit for determining dimensional measurement data of the component from the three-dimensional X-ray image, said component carrier being displaceable along a longitudinal axis for the geometric measurement of the component, said longitudinal axis extending from said radiation source to said planar detector, said planar detector being pivotable about a pivot axis extending transverse thereto, said pivot axis extending from said radiation source to said planar detector.

2. An X-ray computer tomograph according to claim 1, wherein the geometry detection unit is configured in such a way that a component surface of the component is determinable.

3. An X-ray computer tomograph according to claim 2, wherein the geometry detection unit is configured in such a way that the component surface is determinable from connected triangular areas.

4. An X-ray computer tomograph according to claim 1, wherein the component carrier is rotatably drivable about a rotational axis as one degree of freedom of movement.

5. An X-ray computer tomograph according to claim 4, wherein the component carrier is drivable in a translatory manner along the rotational axis as a further degree of freedom of movement.

6. An X-ray computer tomograph according to claim 5, wherein the component carrier is displaceable along a helical trajectory in such a way that a ratio of feed per rotation to beam widening along the rotational axis is less than 1.5.

7. An X-ray computer tomograph according to claim 6, wherein the reconstruction unit is configured in such a way that the X-ray image is reconstructable from the X-radiation detected along a helical trajectory.

8. An X-ray computer tomograph according to claim 5, wherein the component carrier is displaceable along a helical trajectory in such a way that a ratio of feed per rotation to beam widening along the rotational axis is less than 1.

9. An X-ray computer tomograph according to claim 5, wherein the component carrier is displaceable along a helical trajectory in such a way that a ratio of feed per rotation to beam widening along the rotational axis is less than 0.85.

10. An X-ray computer tomograph according to claim 5, wherein the component carrier is displaceable along a helical trajectory in such a way that a ratio of feed per rotation to beam widening along the rotational axis is less than 0.7.

11. An X-ray computer tomograph according to claim 4, wherein the component carrier is pivotable about a pivot axis running transverse to the rotational axis as a further degree of freedom of movement.

12. An X-ray computer tomograph according to claim 11, wherein the reconstruction unit is configured in such a way that the X-ray image is reconstructable from the X-radiation detected along two circular trajectories inclined with respect to one another.

13. An X-ray computer tomograph according to claim 1, wherein the radiation source detector unit is configured in such a way that a radiation source detector spacing is changeable.

14. An X-ray computer tomograph according to claim 1, wherein the radiation source has a cone opening angle of more than 10°.

15. An X-ray computer tomograph according to claim 1, wherein the radiation source has an accelerating voltage of at least 150 kV.

16. An X-ray computer tomograph according to claim 1, wherein the radiation source has a cone opening angle of more than 30°.

17. An X-ray computer tomograph according to claim 1, wherein the radiation source has a cone opening angle of more than 50°.

18. An X-ray computer tomograph according to claim 1, wherein the radiation source has an accelerating voltage of at least 450 kV.

19. An X-ray computer tomograph according to claim 1, wherein the radiation source has an accelerating voltage of at least 900 kV.

20. An X-ray computer tomograph according to claim 1, wherein the component carrier is displaceable along the longitudinal axis such that projections of the component are producible with a desired magnification.

21. An X-ray computer tomograph according to claim 1, wherein the planar detector is pivotable about the pivot axis such that at least one of a line direction and a column direction of the planar detector is oriented with respect to the at least one trajectory.

22. An X-ray computer tomograph according to claim 1, wherein the pivot axis runs perpendicular and centrally with respect to the planar detector such that the pivot axis coincides with the longitudinal axis.

23. A method for examining a component by means of X-ray computer tomography, the method comprising the steps:
positioning a component to be examined on a component carrier between a radiation source and a planar detector of a radiation source detector unit;
displacing said component carrier along a longitudinal axis, and pivoting said planar detector about a pivot axis such that the component is geometrically measurable, said longitudinal axis extending from said radiation source to said planar detector, said pivot axis extending from said radiation source to said planar detector in a direction transverse to said planar detector;
irradiating the component with X-radiation by means of the radiation source, the X-radiation having a three-dimensional radiation geometry;
detecting the X-radiation by means of the planar detector; and
evaluating the detected X-radiation by means of a computing device, wherein:
the radiation source detector unit and the component carry out a movement relative to one another in at least two degrees of freedom of movement, wherein at least one trajectory spanning a three-dimensional space is produced;
a three-dimensional X-ray image of the component is reconstructed from the X-radiation detected along the at least one trajectory by means of a reconstruction unit of the computing device; and
dimensional measurement data of the component are determined from the three-dimensional X-ray image by means of a geometry detection unit of the computing device.

24. A method according to claim 23, wherein the component carrier is displaced along the longitudinal axis such that projections of the component are producible with a desired magnification.

25. A method according to claim 23, wherein the planar detector is pivoted about the pivot axis such that at least one of a line direction and a column direction is oriented with respect to the at least one trajectory.

26. A method according to claim 23, wherein the pivot axis runs perpendicular and centrally with respect to the planar detector such that the pivot axis coincides with the longitudinal axis.

* * * * *